United States Patent
Hårdemark

(10) Patent No.: US 10,300,300 B2
(45) Date of Patent: May 28, 2019

(54) METHOD AND SYSTEM FOR UNCERTAINTY BASED RADIOTHERAPY TREATMENT PLANNING

(71) Applicant: RaySearch Laboratories AB, Stockholm (SE)

(72) Inventor: Björn Hårdemark, Stockholm (SE)

(73) Assignee: RaySearch Laboratories AB, Stockholm (SE)

( * ) Notice: Subject to any disclaimer, the term of this patent is extended or adjusted under 35 U.S.C. 154(b) by 193 days.

(21) Appl. No.: 15/039,670

(22) PCT Filed: Oct. 3, 2014

(86) PCT No.: PCT/SE2014/051147
§ 371 (c)(1),
(2) Date: May 26, 2016

(87) PCT Pub. No.: WO2015/080647
PCT Pub. Date: Jun. 4, 2015

(65) Prior Publication Data
US 2017/0209712 A1    Jul. 27, 2017

(30) Foreign Application Priority Data
Nov. 28, 2013    (EP) .................................... 13194947

(51) Int. Cl.
*G06T 7/11*    (2017.01)
*A61N 5/10*    (2006.01)
*G06T 7/13*    (2017.01)

(52) U.S. Cl.
CPC ......... *A61N 5/1031* (2013.01); *A61N 5/1039* (2013.01); *G06T 7/11* (2017.01); *G06T 7/13* (2017.01); *G06T 2207/10081* (2013.01); *G06T 2207/30096* (2013.01)

(58) Field of Classification Search
None
See application file for complete search history.

(56) References Cited

U.S. PATENT DOCUMENTS

| | | | |
|---|---|---|---|
| 9,694,204 B2* | 7/2017 | Hardemark | A61N 5/1031 |
| 2003/0219098 A1 | 11/2003 | McNutt et al. | |
| 2004/0146141 A1 | 7/2004 | Svatos | |
| 2007/0081629 A1 | 4/2007 | Yin et al. | |
| 2009/0226060 A1* | 9/2009 | Gering | G06T 7/11 |
| | | | 382/128 |
| 2009/0234626 A1* | 9/2009 | Yu | A61N 5/1031 |
| | | | 703/11 |
| 2012/0175530 A1* | 7/2012 | Nord | A61N 5/1031 |
| | | | 250/492.1 |

FOREIGN PATENT DOCUMENTS

| | | |
|---|---|---|
| JP | 2013-132489 A | 7/2013 |
| WO | WO-2007/123913 A1 | 11/2007 |

(Continued)

OTHER PUBLICATIONS

Wei Liu et al., "Robust optimization of intensity modulated proton therapy", Medical Physics, Feb. 2012, vol. 39, No. 2, pp. 1079-1091.

(Continued)

*Primary Examiner* — Tahmina N Ansari
(74) *Attorney, Agent, or Firm* — Drinker Biddle & Reath LLP

(57) ABSTRACT

A method for generating a radiation treatment plan is provided where uncertainties in the definition of regions of interest are incorporated and utilized by a treatment planning system for optimizing a treatment plan.

14 Claims, 3 Drawing Sheets

(56) References Cited

FOREIGN PATENT DOCUMENTS

| WO | WO-2008/120116 A1 | 10/2008 |
| WO | WO-2011/154853 A1 | 12/2011 |
| WO | WO-2012/012768 A1 | 1/2012 |

OTHER PUBLICATIONS

Pavel Stavrev et al., "Inverse treatment planning by physically constrained minimization of a biological objective function", Medical Physics, Nov. 2003, vol. 30, No. 11, pp. 2948-2958.
Witte Marnix et al., "IMRT optimization including random and systematic geometric errors based on the expectation of TCP and NTCP", Medical Physics, Sep. 2007, vol. 34, No. 9, pp. 3544-3555.
International Search Report dated Apr. 1, 2015 for PCT/SE2014/051147.
European Search Report completed May 6, 2014 for EP Patent Application No. 13194947.1.
Gloria Mazzara et al., "Brain Tumor Target volume Determination for Radiation Treatment Planning Through Automated MRI Segmentation," International Journal Radiation Oncology, Biology and Physics, 2004, pp. 300-312, vol. 59, No. 1.
O. Ballivy et al., "Impact of geometric uncertainties on dose distribution during intensity modulated radiotherapy of head-and-neck cancer: the need for a planning target volume and a planning organ-at-risk volume," Current Oncology, 2006, pp. 108-15, vol. 13, No. 3.

* cited by examiner

METHOD AND SYSTEM FOR UNCERTAINTY BASED RADIOTHERAPY TREATMENT PLANNING

CROSS REFERENCE TO RELATED APPLICATIONS

This application is a § 371 National Stage Application of PCT International Application No. PCT/SE2014/051147 filed Oct. 3, 2014, which claims benefit of European Patent Application No. 13194947.1 filed Nov. 28, 2013, both of which are herein incorporated by reference in their entirety.

FIELD OF THE INVENTION

The present invention relates to the field of radiotherapy, and in particular to radiotherapy treatment planning.

BACKGROUND

In radiotherapy, the goal is typically to deliver a sufficiently high dose to a target (for example a tumor) while sparing surrounding normal tissue as far as possible. In particular, it is important to minimize the dose to sensitive organs close to the target. A treatment plan, for example created using a treatment planning system (TPS), defines how each radiotherapy session is to be conducted in order to achieve these treatment goals. More specifically, in inverse treatment planning an optimization algorithm is employed for finding a set of treatment parameters that will generate a dose distribution within the subject that most closely matches the desired dose.

Radiotherapy treatment planning is based on medical images, such as three-dimensional CT images. In order to serve as basis for treatment planning, these images must be segmented. Segmentation of an image refers to the process of defining or reconstructing different internal structures or other regions of interest (ROIs) in an image. These could for example be specific internal organs which are identifiable in the images. Segmented ROIs are often represented as solid or translucent objects in the three-dimensional images so as to be viewable, and possibly also manipulatable, for a user of a treatment planning system.

In the field of radiation treatment planning, regions of interest can be for example target volumes or organs at risk (OARs). The ROIs may be manually delineated and segmented in the images using various tools, such as tools for drawing contours in CT slices. Alternatively, automatic or semi-automatic methods can be used. For example, such methods can employ structure models or atlases comprising already segmented structures which are transferred into the new and not yet segmented medical image and automatically adapted in order to correspond to the geometry of the patient. Such automatically segmented structures are then manually evaluated and approved or modified.

Accurately segmented ROIs are crucial for obtaining high quality treatment plans. Nonetheless, there will always be some degree of uncertainty regarding the extent to which a delineated ROI contour corresponds to the true location of the region. This degree of uncertainty might be different for different parts of a ROI contour. For example, the true location of a certain part of a ROI contour which is located in a low-contrast region (i.e. a region where the density of surrounding tissue is similar to the ROI density) might be more uncertain compared to a part where the ROI border is easily discernible from the surrounding tissue in the image due to high contrast.

Besides contouring uncertainties, other uncertainties regarding the definition of a region of interest might be identified by an oncologist, such as uncertainties whether or not a specified region in fact contains disease, or uncertainties regarding the biological response of tissue in a region.

There is a large inter-observer variability in the definition of tumors and other structures, such that the volumes and other properties of regions defined by one oncologist can differ significantly from those defined by another oncologist. These differences are not necessarily due to varying levels of competence or experience of oncologists, but are often a result of other factors, such as, for example, insufficient image quality (i.e. a precise definition of a ROI is not possible due to low image quality).

Uncertainties relating to organ location and movement, patient setup errors, etc., have traditionally been handled by applying margins to ROIs. As a result, treatment planning is based on enlarged volumes, ensuring adequate dose coverage of targets and/or sufficient sparing of risk organs. However, this is a crude method which potentially leads to treatment plans where a dose higher than necessary is delivered to healthy tissue. More advanced methods based on probabilistic approaches have also been suggested for taking uncertainties with respect to patient setup and organ motion into account during the optimization of a radiotherapy treatment plan. Such methods usually involve consideration of a plurality of more or less probable scenarios, for example defined by different shifts of a target volume.

However, there are still many parameters regarding uncertainties which are not taken into consideration in an appropriate way during treatment planning.

An aim of the present invention is to overcome, or at least mitigate, the drawbacks described above, and in particular to provide a treatment planning system that will enable a more optimal treatment plan to be generated.

SUMMARY

According to one aspect of the invention, a method for generating a radiation treatment plan for a subject on the basis of an internal image of said subject, the method being executed in a computer and comprising the steps of:
retrieving an image of a subject;
retrieving at least one uncertainty measure related to a region of interest in the image, whereby said at least one uncertainty measure reflects a degree of uncertainty regarding the definition of said region of interest; and
generating the radiation treatment plan at least partly on the basis of said at least one uncertainty measure, and whereby the step of generating the radiation treatment plan comprises determining whether or not to treat said region of interest, or part of said region of interest is provided.

According to another aspect of the invention, a computer program product is provided. Preferably, the computer program product comprises computer-readable instructions which, when executed on a computer, will cause the computer to perform the method for generating the radiation treatment plan.

According to yet another aspect of the invention, a computer system is provided. Preferably, the computer system comprises a processor coupled to at least one memory having stored thereon a computer program comprising computer-readable instructions for generating the radiation treatment plan, wherein the processor is configured to execute the computer-readable instructions.

Hence, the invention achieves the aim defined above by incorporating information regarding uncertainties of ROI definition into the treatment planning process. This will enable the treatment planning system to determine a more optimal treatment plan since every necessary trade-off can be assessed in view of related ROI definition uncertainties.

According to some embodiments, the uncertainty measure refers to an uncertainty of the location of a contour, or a part of a contour, of a region of interest. Hence, the uncertainty regarding the delineation of a ROI, which often can be substantial, is incorporated into the process of optimizing a treatment plan. The uncertainty measure could be defined by a contour, or part of a contour, having a greater width in relation to an ordinary contour width, of a region of interest. Thereby, the uncertainty measure could be easily defined using a suitable tool and/or clearly visualized in the image.

According to some embodiments, the uncertainty measure refers to an uncertainty regarding the properties of the tissue within said region of interest. Hence, an uncertainty regarding a property of the tissue which is of importance for the radiation treatment is incorporated into the process of optimizing a treatment plan. Such property could for example relate to the type of tissue within the region. According to some embodiments, the properties of the tissue relates to presence or absence of tumorous cells. Thereby, the probability of (i.e. the risk for) disease being present in a certain region can be utilized for determining a more optimal treatment plan. According to some embodiments, the properties of the tissue relates to biological response. Thereby, an uncertainty in the biological response, i.e. a probability of certain adverse patient effects (or lack thereof) emerging due to presence of tumorous cells, or due to radiation from the treatment, can be estimated (or identified in some other way) and utilized in the treatment planning process.

According to some embodiments, the step of generating a radiation treatment plan comprises determining whether or not to treat a region of interest, or a part of a region of interest. Hence, a treatment plan can be determined where certain target regions, or parts of target regions, are not treated at all. This might be a result of using various region specific uncertainties (for example relating to presence of disease and/or expected biological response) as input to a treatment planning system, and where the risk for some specific unacceptable radiation-induced adverse effect is determined to exceed the risks involved with not treating a specific target region, or part of a target region.

According to some embodiments, the uncertainty measure is based on one or more of: expert input, image data, measurements, statistical data and simulations. Hence, an uncertainty does not necessarily have to be estimated and input by an expert, but can be determined in other ways. However, an uncertainty measure determined in an automatic way would in general be evaluated and approved by an expert before being used in a treatment planning process.

According to some embodiments, a radiation treatment plan is generated at least partly on the basis of an uncertainty measure related to a first region of interest, a first treatment objective or constraint defined in relation to the first region of interest, and a second treatment objective or constraint which at least in part stands in conflict with the first treatment objective or constraint. Thereby, a treatment plan is based on a compromise between conflicting treatment goals, where specified uncertainties regarding the definition of a region being relevant for at least one of the treatment goals are taken into consideration. Hence, a trade-off is assessed both in view of a region definition uncertainty and in view of conflicting treatment goals.

According to some embodiments, generating the radiation treatment plan comprises the steps of maximization of a probability of satisfying one or more clinical goals defined for a region of interest, where said probability at least in part depends on an uncertainty measure. Clinical goals for the radiation treatment are usually defined by a clinician, e.g. an oncologist. By employing a treatment planning process aiming at maximizing the probability of satisfying these goals, any defined uncertainty measure is efficiently incorporated into the process, resulting in a treatment plan having a probability as high as possible to satisfy all goals prescribed by the oncologist. Alternatively or additionally, constraints could be imposed on the probability of satisfying some clinical goals related to one or more ROIs. Thus, in the treatment planning process, other treatment objectives can be optimized instead, subject to these constraints. For example, if using a constraint defining some minimum acceptable probability of satisfying specific goals (where the probability is dependent on defined ROI definition uncertainties), the treatment planning system can determine the best possible treatment plan with respect to other treatment objectives, however still satisfying the predefined constraints on the minimum acceptable probability.

Further aspects of the invention will become apparent by consideration of the detailed description and accompanying drawings. These are only for purposes of illustrating preferred embodiments and are not to be construed as limiting the invention.

DETAILED DESCRIPTION

In FIGS. 2-5, two-dimensional cross sections of diagnostic patient images are shown (i.e. representations of single slices of CT scans). This is merely for illustrative purposes and for facilitating understanding of the invention, and it is emphasized that the diagnostic images usually comprise many slices defining three-dimensional representations of subjects. Accordingly, the regions of interest shown in the figures could be considered cross sectional views of volumes defined in a 3D image of a patient. The 3D representation of a patient can be discretized into a plurality of voxels for the purpose of dose calculation.

Figure 1:
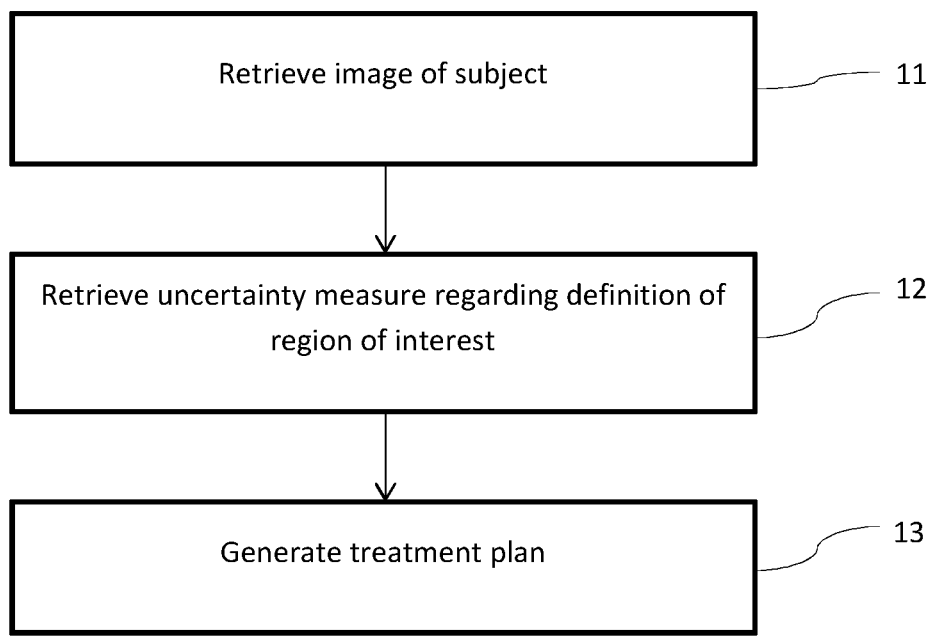
FIG. 1 is a flowchart of a method according to the invention.

FIG. 1 is a flowchart showing the different steps of a method according to the invention.

In step 11, an internal image (i.e. an image showing internal aspects of a body) of a subject is retrieved. This could be a three-dimensional image from a computed tomography (CT) scan, but also other imaging modalities, or combination of modalities, are possible, such as, for example, magnetic resonance imaging (MM).

In step 12, at least one uncertainty measure regarding some aspect relating to the definition of a region of interest in the image is retrieved. For example, the uncertainty measure could relate to presence of disease, biological response, or location of ROI contours. As an example, an uncertainty measure could define a range of possible contour locations. Uncertainty measures might be pre-defined, for example manually by an oncologist, for example during a delineation process, and/or input as feedback during an iterative treatment planning process.

In step 13, the treatment plan is generated taking into account one or more of the uncertainty measures. The treatment plan is generated using a treatment planning system which, in addition to the uncertainty measures, employs a plurality of other parameters for optimizing a treatment plan, such as dose- or biologically based treatment objectives or constraints, as discussed below.

A treatment plan can be optimized for use in any kind of radiation treatment apparatus using any kind of modality including photons, protons or electrons. The treatment plan can be an Intensity Modulated Radiation Therapy (IMRT) plan or any other radiation treatment plan, such as, for example, a Three-Dimensional Conformal Radiation Therapy (3DCRT) plan or a Volumetric Modulated Arc Therapy (VMAT) plan.

A common approach in inverse treatment planning is to minimize (or maximize) an objective function composed of all optimization functions, often subject to certain planning constraints. The objective function can be a weighted sum of all optimization functions $f_i$, i.e., $$f = \sum_i w_i f_i \quad (1)$$

where the weights $w_i$ of the optimization functions correspond to the rates at which a decrease in one optimization function value is traded for an increase in a second optimization function value, relating to another, possibly conflicting, treatment goal. It is possible to use voxel-specific weights reflecting the relative importance of the dose objectives of different voxels in a ROI.

A simple example of an optimization function $f_i$ relating to a ROI comprising j voxels is:

$$f_i = \sum_j \Delta v_j \left( \frac{d_j - d_{ref}}{d_{ref}} \right)^2 \quad (2)$$

where $d_j$ is the dose in voxel j, $d_{ref}$ is the reference dose, and $\Delta v_j$ is the relative volume of voxel j in the ROI. The dose $d_j$ is a function of the treatment parameters which are to be determined by the optimization. The normalization by multiplying with the relative volume $\Delta v_j$ and dividing by the square of the reference dose $d_{ref}$ has the effect that, disregarding objective weights, all ROIs are considered to be equally important irrespective of volume and reference dose level. Using an optimization function as defined in (2), both under- and overdosage with respect to the reference dose are equally penalized. This is only one example, and many other optimization functions can be employed instead of, or in addition to, this function. Examples of such are minimum or maximum dose optimization functions, minimum or maximum dose-volume histogram (DVH) based optimization functions, or radiobiologically based optimization functions.

Various different optimization techniques may be employed when optimizing an objective function to arrive at a treatment plan. For example, gradient-based methods, such as methods based on sequential quadratic programming algorithms, or heuristic methods, such as simulated annealing, can be used. The optimization might be fluence-based, which requires subsequent conversion to machine parameters, or based on Direct Machine Parameter Optimization (DMPO) where machine parameters are directly optimized, or a combination of both. Conventional inverse treatment planning using optimization is well-known in the art and will therefore not be described in further detail herein.

The incorporation of the uncertainty measures into the treatment planning process can be done in various different ways, and this will be discussed below, primarily with reference to FIGS. 3 and 4. By using the inventive method illustrated in FIG. 1, an optimized treatment plan will depend both on the uncertainty measures related to different regions and on the cost (i.e. the extent of necessary trade-offs) for covering (or sparing) these regions.

Figure 2:
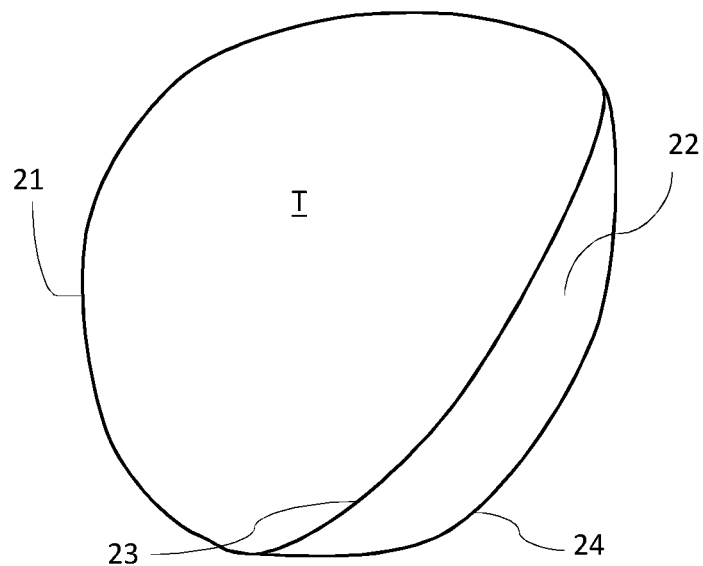
FIG. 2 is a schematic illustration of a target region with an uncertainty measure being defined for a part of the target contour.

FIG. 2 illustrates a 2D representation of a target volume T, having a target contour 21. An uncertainty measure has been assigned to a specific part of the target contour 21, in this case resulting in a widened, "approximate", contour 22, having an inner boundary 23 and an outer boundary 24. Such approximate contour indicates that the true position of the target border is uncertain but is (at least with a high probability) somewhere within the region covered by the approximate contour 22. Thus, the approximate contour reflects an uncertainty of the target definition. The characteristics, such as the width, of the approximate contour 22 could be user-defined, for example by an oncologist during a delineation procedure, or defined in other ways, for example automatically based on image information, as described further below.

The inner boundary 23 of the approximate contour 22 when combined with the remaining part 21 of the target contour defines the smallest target region possible. Correspondingly, the outer border 24 of the approximate contour 22 when combined with the remaining part 21 of the target contour defines the largest target region possible. If achievable, dose should be delivered to the larger target region since there is a possibility that disease is present in the entire region. However, if it is not possible to cover the larger target region without increasing dose to risk organs in an unacceptable way, the coverage of the target region might have to be compromised. Hence, the region defined by the approximate contour 22 indicates where necessary sacrifices in target coverage should primarily be made. For example, if it is possible to cover only the inner half of the region defined by the approximate contour, there is still a chance (although reduced) that all disease will be cured, depending on where the true contour of the target is located.

Hence, by using information regarding the uncertainty, i.e. the extension of the approximate contour, as input for the optimization, a treatment plan can be determined on the basis of additional information which previously has not been available to a treatment planning system.

Figure 3:
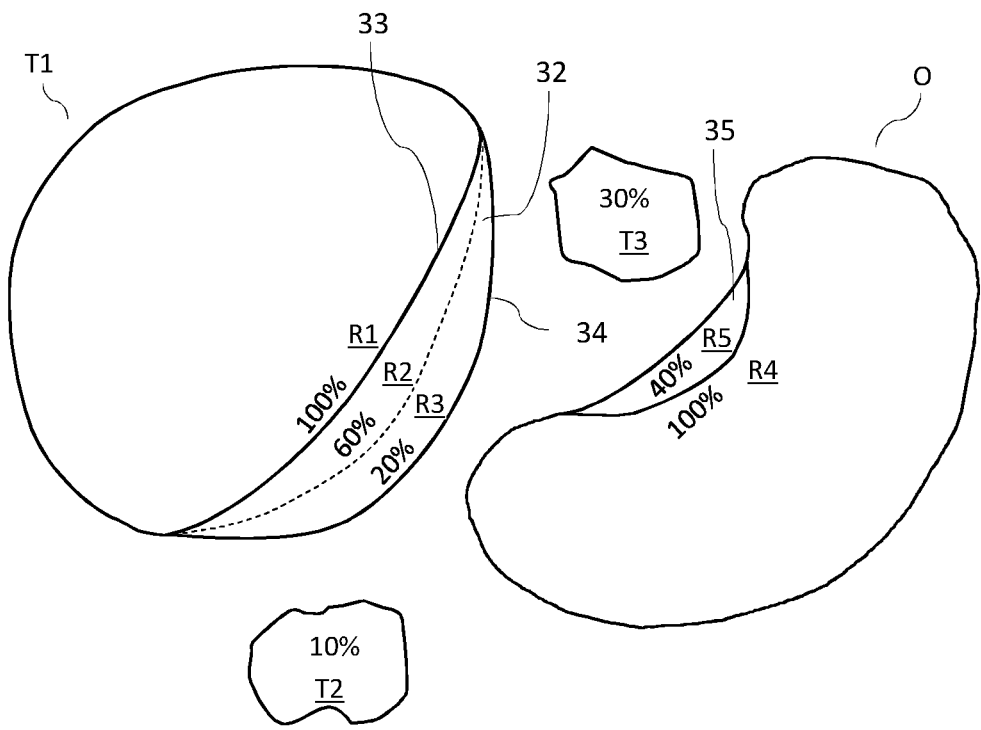
FIG. 3 is a schematic illustration of three separate target regions and a risk organ region, the regions having uncertainty measures defined, which indicate uncertainties of the definition of each region.

FIG. 3 illustrates a 2D image representation of a subject, said image comprising target regions T1, T2, T3 and an organ at risk O. The target region T1 in this example represents a clinical target volume (CTV) where the exact location of a part of the contour is uncertain. The degree of uncertainty is defined in the same way as for the target illustrated in FIG. 2, i.e. using a broad, approximate contour 32, having an inner contour boundary 33 and an outer contour boundary 34, in which somewhere the true target border is located. An uncertainty measure defining a degree of uncertainty with respect to the location of some part of a CTV contour could be seen as an uncertainty regarding the presence of disease in regions close to the CTV border, i.e. a probability that a specific region or voxel contains disease. If considering the smallest possible CTV defined by the inner contour boundary 33 of target T1 as a region $R_1$ with a very high probability of tumor cell presence (i.e. close to 100%), and the regions outside the outer contour boundary 34 of target T1 as regions with a very low probability of tumor cell presence (i.e. close to 0%), the tumor presence probability can be considered to vary between 0 and 1 inside the approximate contour region 32. Hence, each voxel in the approximate contour region 32 can be given a specific disease presence probability in accordance with the voxel position in relation to the approximate contour boundaries. The approximate contour region can be divided in a predetermined amount of regions where each region is assigned a specific disease presence probability in accordance with the distance to the inner and outer boundaries 33, 34 of the approximate contour. According to the embodiment illustrated in FIG. 3, the approximate contour region of the target T1 is divided into two regions $R_2$, $R_3$ where the inner $R_2$ and outer $R_3$ region are assigned a disease presence probability of 60% and 20%, respectively. By modeling the approximate contour as discrete regions having different disease presence probabilities, the uncertainty information can easily be incorporated in treatment plan optimization, as will be described further below.

Uncertainty measures relating to the definition of a region of interest can be directly assigned to a region, for example based on an uncertainty regarding the properties of the tissue within the region, such as an uncertainty regarding the type of tissue and/or regarding a biological response. For example, a probability of presence of disease (e.g. tumorous cells) can be assigned to specific regions, such as regions of suspected metastases (i.e. regions where disease is possible but not confirmed). Alternatively or additionally, a probability which is based on an uncertainty in the expected biological response could be assigned to a region. For example, such probability, when defined for a target region containing disease, could be an estimated risk of some specified adverse patient effect occurring due to the disease, e.g. a risk of patient non-survival, if not being treated. Correspondingly, when defined for a risk organ, the uncertainty regarding biological response could relate to an estimated risk of some specific adverse effect occurring as a result of receiving a specified amount of radiation dose.

Uncertainty measures regarding the properties of tissue could be based on expert opinions, such as estimations by an oncologist, or on measurements, e.g. based on biopsies or PET scans, or on computer simulations and/or statistical data from other patients, etc.

In FIG. 3, specific tumor presence probabilities have been assigned to target regions T2 and T3, which in this case represent regions where metastases might be present. According to this example, and as indicated in the figure, the target region T2 has a disease presence probability of 10% while the target region T3 has a disease presence probability of 30%, the probabilities for example estimated by an oncologist. The probabilities indicated in the figures thus represent a probability that at least one voxel within the respective regions contain disease. In an alternative exemplary embodiment, assuming that presence of disease in the regions T2 and T3 is confirmed, the uncertainty measures for regions T2 and T3 could be based on an expected biological response. Hence, according to such an embodiment, the probabilities defined for regions T2 and T3 could be probabilities of some unwanted patient effect, such as the patient not surviving, if the regions are not treated. Hence, as an example, the uncertainty measure defined for the region T2 would correspond to a probability of 90% that the patient survives even if the region T2 is not treated.

In the following examples relating to FIG. 3, the probabilities defined for regions T2 and T3 are described as probabilities of presence of disease, but it is to be understood that probabilities of these kinds just as well could reflect uncertainties regarding biological response (i.e. not specifically considering presence or absence of tumorous cells) as described above.

Also the contour of the risk organ O has a part of which the actual location is uncertain, defined by a relatively wider, approximate, contour segment 35. Analogous to considering the probability of tumor presence in the uncertain region of target T1, the approximate contour 35 of the risk organ O reflects a probability of voxels actually containing tissue cells which are specific for the risk organ. Accordingly, a voxel within the approximate contour region 35 of the risk organ O is assigned a probability that the voxel in fact contains OAR tissue. In the simplified example illustrated in FIG. 3, the uncertainty is modeled using a single constant probability (40%) resulting in one region $R_4$ with 100% probability and another region $R_5$ with 40% probability.

The uncertainty measures, in this example in the form of probabilities for disease presence or presence of OAR tissue, are used as input to a treatment planning system. One obvious method for incorporating the region specific probabilities would be to define a set of corresponding region or voxel specific importance weights used in the optimization algorithm, so that voxels in regions which are more "certain" are given higher weights in the optimization. However, such approach would generally not be suitable. For example, considering a target region, a treatment plan optimized on the basis of such an objective function would still deliver dose to all parts of the uncertain regions, although with reduced dose levels. This would in general not be a satisfactory result since all parts containing disease must receive a certain amount of dose in order for tumor control to be achieved. That is, all parts of a target where the clinical goals are possible to satisfy should be covered with the prescribed dose. Hence, to parts of a target where an uncertainty exists regarding presence of disease, and where the clinical goals are impossible to satisfy without violating other important treatment objectives, dose should rather not be delivered at all. Accordingly, other, generally more advantageous, methods for incorporating the uncertainty information are discussed below.

As a simple example, a plurality of different treatment plans can be determined, where different combinations of regions involving different specified uncertainty measures are considered in separate scenarios. For example, different treatment plan candidates can be evaluated based on uncertainty measures related to covered regions within the target, and the fulfillment of target objectives (e.g. relating to a prescribed minimum dose) in the respective regions, in view of fulfillment of various other conflicting optimization objectives or constraints, for example relating to risk organ sparing. Hence, as an example, the plan which results in the highest probability of achieving tumor control (as determined based on the uncertainty measures) while also not exceeding specified dose tolerance levels for risk organs, is automatically selected.

In the following, three examples of how to incorporate ROI definition uncertainties in the treatment planning process are described in more detail, with reference to FIGS. 3 and 4.

Example 1—Discrete Regions

Consider a ROI with regions $R_1, \ldots, R_n$ that have probabilities $p_1, \ldots, p_n$ of containing disease. Each region $R_i$ for i>1 is dependent on the regions $R_j$ for all j>i in the sense that there is no benefit of satisfying clinical goals in region $R_i$ before the clinical goals are satisfied in the regions $R_j$ for j<i.

For the target T1 in FIG. 3, these regions are $R_1$, $R_2$, and $R_3$, where $R_1$ is the region with 100% probability of containing disease, $R_2$ the region with 60% probability of containing disease, and $R_3$ the region with 20% probability of containing disease. Thus, $p_1=1$, $p_2=0.6$, and $p_3=0.2$. The dependence between the regions implies that given a clinical goal for the target T1, one should first strive towards satisfying the goal in the region $R_1$, then in the region $R_1 \cup R_2$, and then in the region $R_1 \cup R_2 \cup R_3$. This means that if the goal is to deliver a dose of 50 Gy to target T1, there is no benefit of delivering 50 Gy to the region $R_3$ unless the region $R_1 \cup R_2$ receives 50 Gy, and there is no benefit of delivering 50 Gy to the region $R_2$ unless the region $R_1$ receives 50 Gy. As would be apparent to the skilled person, in an alternative embodiment it would be possible to consider the different regions as mutually independent.

The probability of satisfying the clinical goal (e.g. a minimum dose to a target region) in a given ROI with dependent regions $R_1, \ldots, R_n$ can be calculated according to the following:

Consider the regions $R_1, R_1 \cup R_2, R_1 \cup R_2 \cup R_3, \ldots, \cup_{i=1}^n R_i$ in order. If the clinical goals are satisfied for all of these, then the probability of satisfying the clinical goals is 1. Otherwise, let j denote the index of the first one of these for which the clinical goals are not satisfied, i.e. the clinical goals are not satisfied in the region $\cup_{i=1}^j R_i$. The probability that there is disease in this region is the minimum probability of its constituents, i.e., min $\{p_1, \ldots, p_j\} = p_j$, where the equality is due to that the regions are ordered in decreasing order of probability. Thus, the probability that the clinical goals will not be satisfied is $p_j$.

Accordingly, as an example with reference to FIG. 3, assume that the clinical goals are satisfied in the region $R_1$ of target T1, but not in the region $R_1 \cup R_2$ (and hence neither in the region $R_1 \cup R_2 \cup R_3$). Then $R_1 \cup R_2$ is the first region for which the clinical goals are not satisfied, which implies that there is a probability of $p_2=0.6$ of not satisfying the clinical goals for target T1. Furthermore, all targets T1, T2, and T3, as illustrated in FIG. 3, are all mutually independent. As an example, assume that the clinical goals are not satisfied for target T2, but that they are satisfied for target T3. Then there is a probability of 0.1 of not satisfying the clinical goals of target T2 (since there is a 10% probability that there is disease in target T2) and a probability of 0 of not satisfying the clinical goals of target T3. The total probability of curing all tumors is then: $(1-0.6) \times (1-0.1) \times (1-0) = 0.36$.

Similarly, the probability of satisfying the goals for various OARs, such as the region O in FIG. 3, can be computed. The optimization should then find the plan that performs the best with respect to these probabilities. For example, it could strive for maximizing the product of all probabilities (i.e. the probability of satisfying all clinical goals). Alternatively, constraints could be imposed on one or more of the probabilities and some other goals be optimized (such as, for example, treatment objectives relating to max dose, number of monitor units (MUs), etc.).

Using an optimization as described above, the trade-offs will depend on the uncertainty measures of the respective regions, as well as the cost of achieving dose coverage/sparing of the different regions. As an example, with reference to FIG. 3, assume that it is possible to satisfy the clinical goals in regions $R_1$ of target region T1 as well as in target region T3 (resulting in a probability to satisfy the target clinical goals of 0.36 as exemplified above) while simultaneously satisfying the clinical goals for both of the regions $R_4$ and $R_5$ of the OAR O (i.e. resulting in a probability to satisfy the OAR clinical goals of 1). This would result in a probability to satisfy all clinical goals of $0.36 \times 1 = 0.36$. Now, assume that if the OAR clinical goals in region $R_4$ but not in region $R_5$ are satisfied (resulting in a probability to satisfy the OAR clinical goals of $1-0.4=0.6$), it is possible to satisfy the target clinical goals not only in region $R_1$ and target T3 but also in region $R_2$ (resulting in a probability to satisfy the target clinical goals of $(1-0.2) \times (1-0.1) \times (1-0) = 0.72$). This would result in a probability to satisfy all clinical goals of $0.72 \times 0.6 = 0.432$.

Hence, the probability of satisfying all clinical goals is maximized using a treatment plan where dose is prescribed to regions $R_1$, $R_2$ and T3 but not to regions $R_3$ and T2, indicating that it is not beneficial to plan dose to the target regions $R_3$ and T2 since this is too expensive in terms of sparing the risk organ O.

By considering all available uncertainty information, a treatment planning system will identify the most beneficial trade-offs in specific situations, resulting in a better treatment plan, e.g. yielding the highest possible probability of achieving total tumor coverage without normal tissue complications.

Example 2—Continuous and Non-Hierarchical Regions

Consider a target region R within which each point has a prescribed probability in the interval (0, 1] of containing disease. The aim of the optimization is to maximize the probability of curing the disease.

For a goal that is separable per voxel (e.g., a goal that the dose to each voxel should be above 60 Gy), the probability of satisfying the goal in all voxels with disease (delivering dose above 60 Gy to all voxels with disease) can be calculated as $$\prod_{i \in I} (1 - p_i) \qquad (3)$$

where I is the set of all voxels belonging to the region R for which the goal is not satisfied (the voxels in R with dose below 60 Gy) and $p_i$ is the probability that voxel i contains disease. If the set I is empty, the probability is 1.

The goal of the optimization is to deliver a dose that maximizes this probability, which is the same as delivering dose in such a way that there is as low probability as possible that the voxels in the set I contain disease.

It may be desirable to treat a connected target volume. This can be achieved by the introduction of constraints on the shape of the volume to be treated so that the treated target volume is always a connected volume.

Figure 4A:
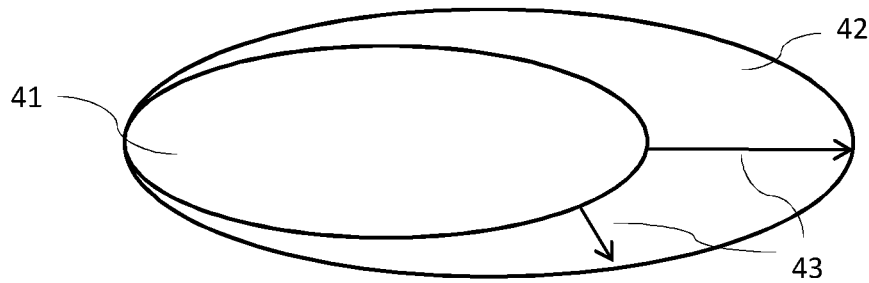
FIG. 4A schematically illustrates a target region with an uncertainty measure being defined as a region with continuously varying probabilities of disease presence.

FIG. 4A illustrates a 2D image representation of a target volume comprising an inner region 41 where disease is known to be present and an outer "uncertain" region 42, reflecting the target definition uncertainty. Hence, the region 42 could correspond to an approximate contour, for example defined by an expert, similarly to the examples described above. The voxels inside the inner region 41 are considered to have 100% probability of containing disease while voxels outside the regions 41 and 42 are considered as having 0% probability of containing disease. Accordingly, each voxel within the outer region 42 has a probability ranging from 0 to 1 of containing disease. The probability for a voxel can depend on the position of the voxel within the outer region 42. For example, the probabilities can decrease linearly, or exponentially, from 1, for voxels at the inner border of the outer region 42, to 0, for voxels at the outer border of the outer region 42, along normals 43 to the surface of the inner region 41. Obviously, varying probabilities within the outer region 42 can be defined in many other ways, for example in accordance with estimations made by an expert. For example, multiple regions of differently continuously varying probabilities can be defined.

Figure 4B:
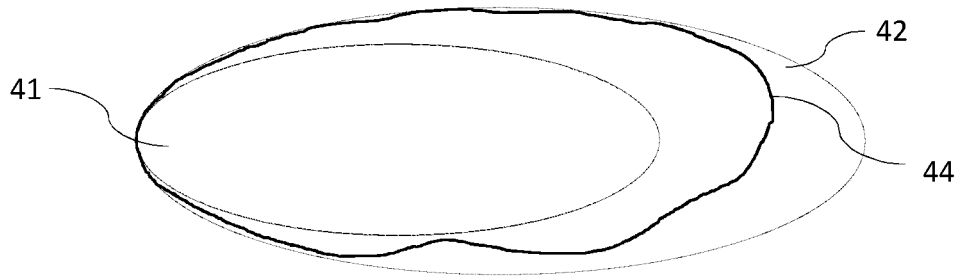
FIG. 4B schematically illustrates a region to be treated as determined during treatment planning based on the defined uncertainties.

Using equation (3) in a method as described above, the treated target volume is maximized. FIG. 4B illustrates an exemplary target volume 44 resulting from using such method. As seen in the figure, the treated volume can have some degree of irregularity. However, for similar reasons as discussed above in view of example 1, it might be advantageous to impose constraints on the shape of the target volume since it would not usually be useful to treat a distant region if an adjacent region closer to the target center is not treated.

Example 3—Non-Separable Goals

As before, consider a region R within which each voxel has a prescribed probability in the interval (0, 1] of containing disease (if the region relates to a target) or, if the region relates to an OAR, some other tissue type specific for the region. In the following, the region R is exemplified as relating to a target region. Accordingly, the probability assigned to a voxel reflects the probability that the true target volume contains the voxel, and hence, the probabilities decrease from 100% for voxels in the region known to contain disease to 0% for voxels in the region known not to contain disease. Consider all possible target volumes and, for each of these, a corresponding probability of it being the true target volume (these are nonzero because of the discretization into voxels). The voxels with 100% probability will be contained in all of these target volumes. Given a plan, let S be the index set over all of the target volumes for which the clinical goals are satisfied, and let $p_i$ be the probability of the target volume $i \in S$ being the true target volume. The goal of the optimization is then to maximize the probability of satisfying the clinical goals in the true target volume, which means maximizing $$\sum_{i \in S} p_i \quad (4)$$

This is achieved by finding the dose distribution that results in a region S that indexes a set of target volumes that is as probable as possible to contain the true target volume.

This approach is applicable when using goals which are not separable per voxel, for example when using DVH based optimization functions (i.e. goals demanding that X percent of a ROI receive at least Y Gy).

All the embodiments described above are merely examples of how to incorporate ROI definition uncertainties in the treatment planning process, and many alternative methods are envisaged, as would be apparent to a person skilled in the art.

As mentioned above, it is possible to define ROI definition uncertainties in various different ways. For example, as also discussed above, sub-regions and corresponding uncertainty measures can be manually defined, modified and/or approved, for example by an expert user (e.g. an oncologist) during or after a manual or automatic segmentation procedure. The regions and/or corresponding uncertainty measures could be defined directly in the images using any suitable user interface, for example comprising tools for defining contour segments indicating different degrees of uncertainties (e.g. different contour widths).

The user could also assign numerical measures of uncertainty to a specific part of a contour, the numerical measures for example defining confidence intervals on each side of the contour segment. Numerical uncertainty measures of various kinds, e.g. assigned by an expert, can, possibly in combination with image information, be used to define multiple sub-regions corresponding to the sub-regions discussed above and illustrated in FIG. 3 or for defining continuously varying uncertainties within a specific region, as discussed above and exemplified in FIG. 4A.

The approximate contour regions illustrated in FIG. 3 could be divided into a much larger set of smaller sub-regions, with different assigned probabilities, in order to provide a better basis for treatment planning (although also rendering the treatment planning process more computationally demanding). The number of regions and the corresponding assigned probabilities could be determined automatically according to predetermined criteria. For example, a fixed, predetermined, number of sub-regions can be used, or the number of sub-regions may depend on the extension (e.g. width) of an approximate contour segment. The uncertainty measure of a specific voxel would then depend on the predetermined criteria and the relative distance from the voxel to the inner and outer border of the approximate contour. Alternatively, other methods for defining sub-regions and corresponding uncertainty measures may be employed, such as methods based on analysis of image intensity data. For example, all parts of a defined contour can be assigned an uncertainty measure based on contrast in a region in the vicinity of the respective contour parts. Thus, contour segments in low-contrast regions are automatically assigned a relatively greater uncertainty. Such automatically assigned uncertainty measures are advantageously assessed and approved, or if necessary modified, by an expert.

An uncertainty measure might be visualized in the image in various ways, for example using different sizes, colors, transparency, etc., of elements relating to a ROI. Uncertainty information, e.g. relating to whether specified regions contain disease, can also be determined from measurements (e.g. based on biopsies or PET scans etc.), computer simulations, statistical data from other patients, or in any other way.

Figure 5:
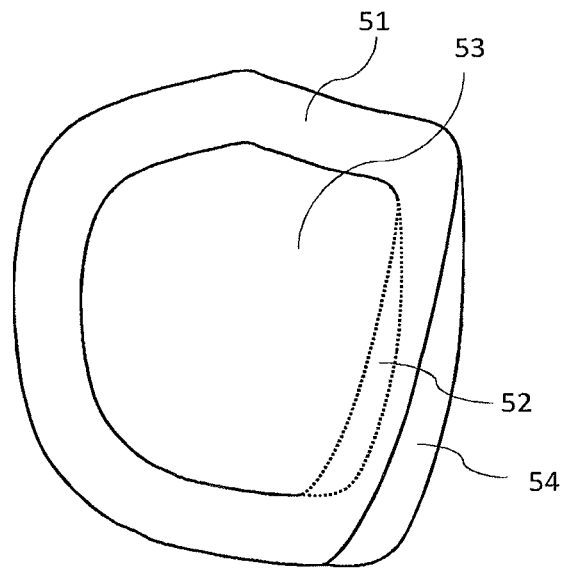
FIG. 5 schematically illustrates an uncertainty measure defined for a CTV transferred to a corresponding PTV.

The methods according to the invention can be combined with any previously used method for generating a more robust treatment plan, such as methods based on probabilistic approaches for taking setup uncertainties into consideration. Furthermore, the inventive methods can be employed on any region, such as a region which has been expanded using a safety margin. A margin is normally applied to a target volume (creating a "planning target volume" (PTV)) in order to compensate for possible setup uncertainties or target movement during treatment. For example, if specific uncertainty measures have been assigned to regions of a clinical target volume (CTV), and a uniform margin is applied to the CTV, defining a PTV, the same uncertainty measures can be assigned to corresponding regions of the PTV and used in the treatment planning process as described above. FIG. 5 shows such a PTV 51 where an approximate contour segment 52 of the CTV 53 is transferred to a corresponding approximate contour segment 54 of the PTV.

Figure 6:
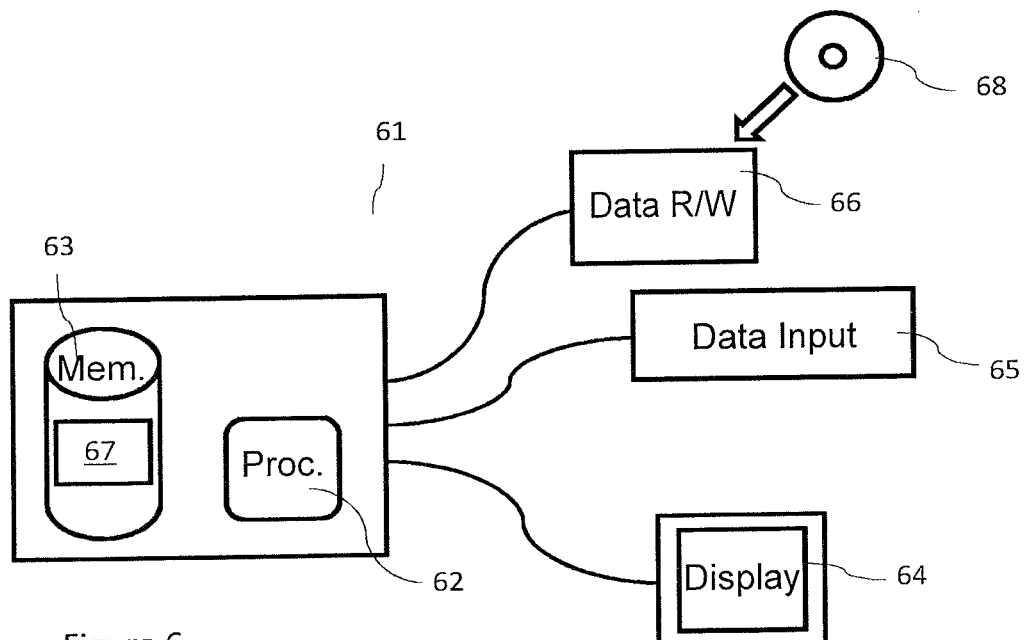
FIG. 6 is a schematic illustration of a computer system according to an example embodiment of the invention.

FIG. 6 schematically illustrates an example of a computer system 61 according to the invention. The system comprises a processor (Proc.) 62, coupled to a memory (Mem.) 63. Furthermore, the system can include a display device 64 (e.g. for displaying patient images with defined ROIs and corresponding uncertainty measures, a graphical user interface, and other information related to treatment planning), a data input device 65 (e.g. a keyboard, a mouse or any other suitable device for data input) and a data reading/writing (Data R/W) device 66 (e.g. an optical drive, USB interface, or any other suitable device for reading/writing data). The processor 62 can be of any kind, such as one or more central processing units (CPU) or any kind of parallel processor system, e.g. based on one or more graphics processing units (GPU). The memory 63 can be any kind of volatile or non-volatile memory suitable for storing and retrieving information, such as, for example, a hard drive. The memory 63 has a computer program 67 stored thereon. The computer program 67 comprises computer-readable instructions for performing uncertainty based optimization where the computer-readable instructions can be transferred to, and executed by, the processor 62. When executed by the processor 62, the computer-readable instructions will perform a method as illustrated in FIG. 1 for determining a treatment plan on the basis of uncertainties in the definition of ROIs. The determined treatment plan can be stored, together with the patient image, the ROIs, the uncertainty measures and any other treatment planning related information on the memory 63. The computer program 67 can also be stored on a non-transitory computer readable medium 68, e.g. a USB drive, an optical data carrier such as a CD-ROM, or any other suitable portable information storage device, so that the computer program 67 can be loaded to the memory 63 and/or transferred to different computing systems. The system described with reference to FIG. 6 is merely an example, and a computer system according to the invention does not necessarily comprise all the illustrated components, and/or might comprise other components not illustrated.

The invention has been described with reference to a number of example embodiments. It is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for generating a radiation treatment plan for a subject on the basis of an internal image of said subject, the method being executed in a computer and comprising the steps of:
retrieving an image of a subject;
retrieving at least one uncertainty measure related to a region of interest in the image, wherein said at least one uncertainty measure reflects a degree of uncertainty regarding the definition of said region of interest;
generating a plurality of different treatment plans, wherein a first subset of the different treatment plans is generated assuming said region of interest or part of said region of interest is not treated and a second subset of the different treatment plans is generated assuming said region of interest or part of said region of interest is treated; and
generating the radiation treatment plan at least partly on the basis of said at least one uncertainty measure, and whereby the step of generating the radiation treatment plan comprises determining whether or not to treat said region of interest, or part of said region of interest, on the basis of the first subset and the second subset of the different treatment plans.

2. The method according to claim 1, wherein said uncertainty measure refers to an uncertainty of the location of a contour, or a part of a contour, of said region of interest.

3. The method according to claim 2, wherein said uncertainty measure is defined by a contour, or part of a contour, having a greater width in relation to an ordinary contour width, of said region of interest.

4. The method according to claim 1, wherein said uncertainty measure refers to an uncertainty regarding the properties of the tissue within said region of interest.

5. The method according to claim 4, wherein the properties of the tissue within said region of interest relates to presence or absence of tumorous cells.

6. The method according to claim 4, wherein the properties of the tissue within said region of interest relates to biological response.

7. The method according to claim 6, wherein said biological response is with respect to presence of tumorous cells.

8. The method according to claim 6, wherein said biological response is with respect to received radiation.

9. The method according to claim 1, wherein said uncertainty measure is based on one or more of:
expert input,
image data,
measurements,
statistical data, and
simulations.

10. The method according to claim 1, wherein the radiation treatment plan is generated at least partly on the basis of an uncertainty measure related to a first region of interest, a first treatment objective or constraint defined in relation to said first region of interest, and a second treatment objective or constraint which at least in part stands in conflict with said first treatment objective or constraint.

11. The method according to claim 10, wherein generating the radiation treatment plan comprises maximization of a probability of satisfying one or more clinical goals defined for one or more regions of interest comprising said first region of interest, and where said probability at least in part depends on said uncertainty measure.

12. The method according to claim 10, wherein said first treatment objective or constraint is a constraint on the probability of satisfying one or more clinical goals defined for said first region, where said probability at least in part depends on said uncertainty measure, and where generating the radiation treatment plan further comprises optimization of said second treatment objective.

13. A computer program product comprising non-transitory computer-readable instructions which, when executed on a computer, causes the computer to perform a method according to claim 1.

14. A computer system comprising a processor coupled to at least one memory having stored thereon a computer program comprising non-transitory computer-readable instructions, said processor configured to, by executing said computer-readable instructions, perform a method according to claim 1.

* * * * *